(12) United States Patent
Karapasha

(10) Patent No.: US 7,081,110 B2
(45) Date of Patent: Jul. 25, 2006

(54) APPLICATOR HAVING AN INDENTED FINGERGRIP WITH RAISED PORTIONS

(75) Inventor: Nancy Karapasha, Monfort Heights, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 300 days.

(21) Appl. No.: 10/621,709

(22) Filed: Jul. 17, 2003

(65) Prior Publication Data

US 2005/0015041 A1    Jan. 20, 2005

(51) Int. Cl.
*A61F 13/20*    (2006.01)
(52) U.S. Cl. .................. 604/904; 604/15; 604/385.17; 604/11; D24/141; 600/29
(58) Field of Classification Search ............ 604/11–18, 604/904, 59, 385.17; 600/29; 206/529; D24/141; 424/430–431
See application file for complete search history.

(56) References Cited

U.S. PATENT DOCUMENTS

| | | | |
|---|---|---|---|
| 2,489,502 A | 11/1949 | Ruth | |
| 3,351,060 A | 11/1967 | Woskin | |
| 3,628,533 A | 12/1971 | Loyer | |
| 3,831,605 A | 8/1974 | Fournier | |
| 3,895,634 A | 7/1975 | Berger | |
| 4,536,178 A * | 8/1985 | Lichstein et al. ............. | 604/15 |
| 4,573,963 A | 3/1986 | Sheldon | |
| 4,573,964 A | 3/1986 | Huffman | |
| 4,891,042 A | 1/1990 | Melvin | |
| 5,290,501 A | 3/1994 | Klesius | |
| 5,346,468 A * | 9/1994 | Campion et al. ............. | 604/13 |
| 5,389,067 A * | 2/1995 | Rejai ........................... | 604/14 |
| 5,395,308 A * | 3/1995 | Fox et al. ..................... | 604/15 |
| 6,045,526 A * | 4/2000 | Jackson ....................... | 604/15 |
| 6,302,861 B1 | 10/2001 | Tweddell, III et al. | |
| 6,413,247 B1 | 7/2002 | Carlucci | |
| 6,423,025 B1 | 7/2002 | Buzot | |
| 6,478,764 B1 | 11/2002 | Suga | |
| 6,890,324 B1 | 5/2005 | Jackson et al. | |
| 2003/0236161 A1 | 12/2003 | Fedyk et al. | |
| 2003/0236485 A1* | 12/2003 | Fedyk et al. ................... | 604/11 |
| 2005/0070839 A1 | 3/2005 | Jackson et al. | |

FOREIGN PATENT DOCUMENTS

| | | |
|---|---|---|
| FR | 2 572 930 | 5/1986 |
| GB | 684290 | 12/1952 |
| GB | 2 166 656 A | 5/1986 |
| GB | 2166656 A * | 5/1986 |

(Continued)

OTHER PUBLICATIONS

PCT International Search Report dated Nov. 17, 2004.

*Primary Examiner*—Tatyana Zalukaeva
*Assistant Examiner*—L C Hill
(74) *Attorney, Agent, or Firm*—Bridget Murray; Kevin C. Johnson; David M. Weirich

(57) ABSTRACT

A tampon applicator including an insertion member adapted to house an absorbent tampon and receive a plunger. The insertion member has an outer surface and a fingergrip region disposed about the outer surface. The fingergrip region includes an indention region having a depth dimension X. The indention region includes raised portions has a height dimension Y, the height dimension Y being less than or equal to the depth dimension X.

20 Claims, 2 Drawing Sheets

FOREIGN PATENT DOCUMENTS

| | | |
|---|---|---|
| WO | WO 99/04741 | 2/1999 |
| WO | WO 03/002048 A1 | 1/2003 |
| WO | WO 03/026529 A2 | 4/2003 |
| ZA | 777411 | 12/1977 |

* cited by examiner

APPLICATOR HAVING AN INDENTED FINGERGRIP WITH RAISED PORTIONS

FIELD OF THE INVENTION

The present invention relates to an insertion device capable of housing an insertable element having an improved fingergrip region to improve the consumer's ability to securely hold the applicator during insertion of an insertable element.

BACKGROUND OF THE INVENTION

As known in the art, applicators are used to both house materials intended to be inserted in a body cavity, such as a tampon or medicaments and to expel the material into the intended orifice. Typically applicators comprise an insertion member and a plunger. The material to be expelled from the applicator, such as an absorbent tampon, is positioned within the insertion member. The insertion member has a first end for insertion of the tampon and a second end for receipt of the plunger. To use the applicator, the consumer will position the first end appropriately, grasp the insertion member, and move the plunger in the insertion member towards the first end to insert the tampon. Some applicators also include a fingergrip configuration that is located on the insertion member, which allows the consumer to more securely hold the applicator during insertion of a material into the body cavity.

Various fingergrip configurations have been proposed to facilitate the handling of the applicator and to improve the insertion experience. One approach is a tampon applicator having an integral fingergrip that is formed by embossing the outside surface of the insertion member of the tampon applicator. The embossed portion of the applicator may take the form of a series of circumferential rings or a series of discrete raised dots. Examples of such fingergrips can be found in U.S. Pat. No. 6,045,526 issued to Jackson; U.S. Pat. No. 5,395,308 issued to Fox, et al.; U.S. Pat. No. 5,290,501 issued to Klesius; U.S. Pat. No. 4,573,964 issued to Huffman; U.S. Pat. No. 4,573,963 issued to Sheldon; U.S. Pat. No. 4,891,042 issued to Nelvin, et al.; U.S. Pat. No. 4,412,833 issued to Weigner, et al.; U.S. Pat. No. 3,895,634 issued to Berger; U.S. Pat. No. 3,628,533 issued to Berger; U.S. Pat. No. 3,628,533 issued to Leyer; U.S. Pat. No. 2,922,423 issued to Rickard; U.S. Pat. No. 2,587,717 issued to Fourness; and U.S. Pat. No. 2,489,502 issued to Ruth.

Another approach to the gripping problem is found in U.S. Pat. No. 3,575,169 issued to Voss, et al., which provides separate raised elements that are applied to an outer tube of a tampon applicator to provide a fingergrip. The elements can be formed of plastic, rubber, ceramic, or other materials, and can be affixed to the outer tube by interference fit or by bonding.

While many have tried to design and manufacture tampon applicators having these improved qualities, there still remains a need for a tampon applicator that has gripping features that provide limited resistance to finger slip during the insertion and the expulsion of the tampon applicator.

SUMMARY OF THE INVENTION

The present invention comprises a tampon applicator comprising an insertion member adapted to house an absorbent tampon and receive a plunger. The insertion member has an outer surface and a fingergrip region disposed about the outer surface. The fingergrip region comprises an indention region having a depth dimension X. The indention region comprises raised portions having a height dimension Y, the height dimension Y is less than or equal to the depth dimension X.

DETAILED DESCRIPTION OF THE INVENTION

Figure 1:
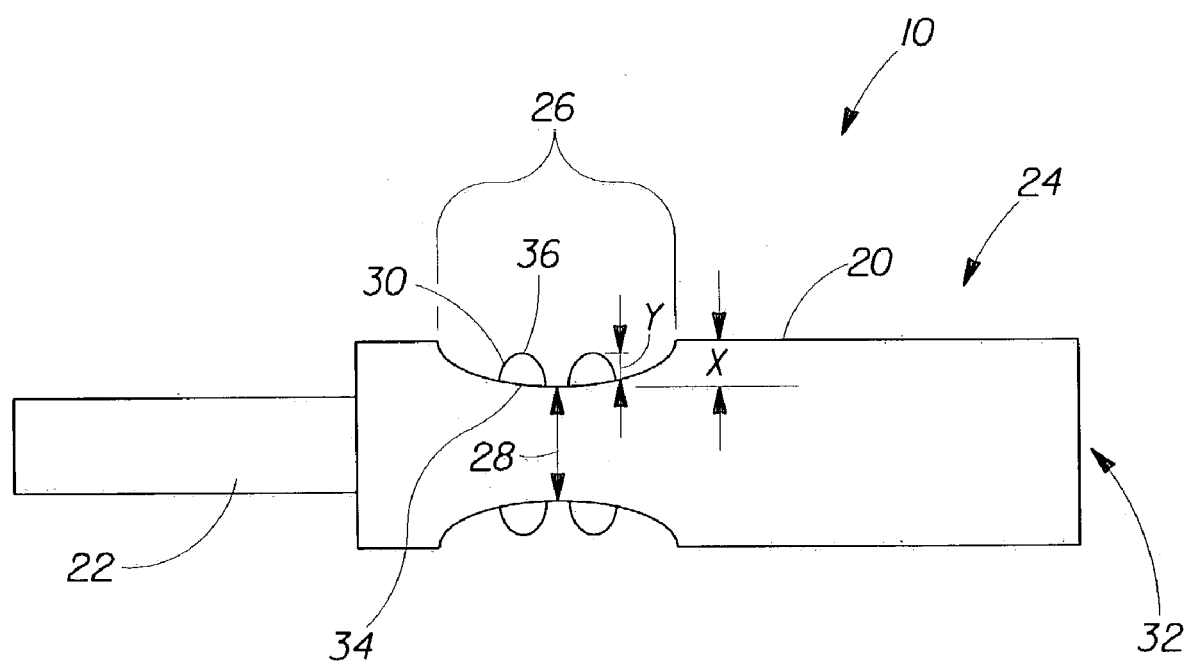
FIG. 1 is a side view of the applicator of the present invention.

As used herein "applicator" refers to a device or implement that facilitates the insertion of a tampon, medicament, treatment device, visualization aid, or other into an external orifice of a mammal, such as the vagina, rectum, ear canal, nasal canal, or throat. Non-limiting specific examples of such include any known hygienically designed applicator that is capable of receiving a tampon may be used for insertion of a tampon, including the so-called telescoping, tube and plunger, and the compact applicators, an applicator for providing medicament to an area for prophylaxis or treatment of disease, a spectroscope containing a microcamera in the tip connected via fiber optics, a speculum of any design, a tongue depressor, a tube for examining the ear canal, a narrow hollow pipe for guiding surgical instruments, and the like.

The term "joined" or "attached," as used herein, encompasses configurations in which a first element is directly secured to a second element by affixing the first element directly to the second element; configurations in which the first element is indirectly secured to the second element by affixing the first element to intermediate member(s) which in turn are affixed to the second element; and configurations in which the first element is integral with the second element; i.e., the first element is essentially part of the second element.

As used herein the term "tampon," refers to any type of absorbent structure that is inserted into the vaginal canal or other body cavities for the absorption of fluid and/or gas therefrom, to aid in wound healing, or for the delivery of active materials, such as medicaments, or moisture. The tampon may be compressed into a generally cylindrical configuration in the radial direction, axially along the longitudinal axis or in both the radial and axial directions. While the tampon may be compressed into a substantially cylindrical configuration, other shapes are possible. These may include shapes having a cross section that may be described as rectangular, triangular, trapezoidal, semi-circular, hourglass, serpentine, or other suitable shapes. Tampons have an insertion end, withdrawal end, a length, a width, a longitudinal axis and a radial axis. The tampon's length can be measured from the insertion end to the withdrawal end along the longitudinal axis. A typical compressed tampon for human use is 30–60 mm in length. A tampon may be straight or non-linear in shape, such as curved along the longitudinal axis. A typical compressed tampon is 8–20 mm wide. The width of a tampon, unless otherwise stated in the specification; corresponds to the length across the largest cylindrical cross-section, along the length of the tampon.

The term "vaginal cavity," "within the vagina," and "vaginal interior," as used herein, are intended to be synonymous and refer to the internal genitalia of the mammalian female in the pudendal region of the body. The term "vaginal cavity" as used herein is intended to refer to the space located between the introitus of the vagina (sometimes referred to as the sphincter of the vagina or hymeneal ring,) and the cervix. The terms "vaginal cavity," "within the vagina" and "vaginal interior," do not include the interlabial space, the floor of vestibule or the externally visible genitalia.

As used herein, "cm" is centimeters, and "mm" is millimeters.

Figure 2:
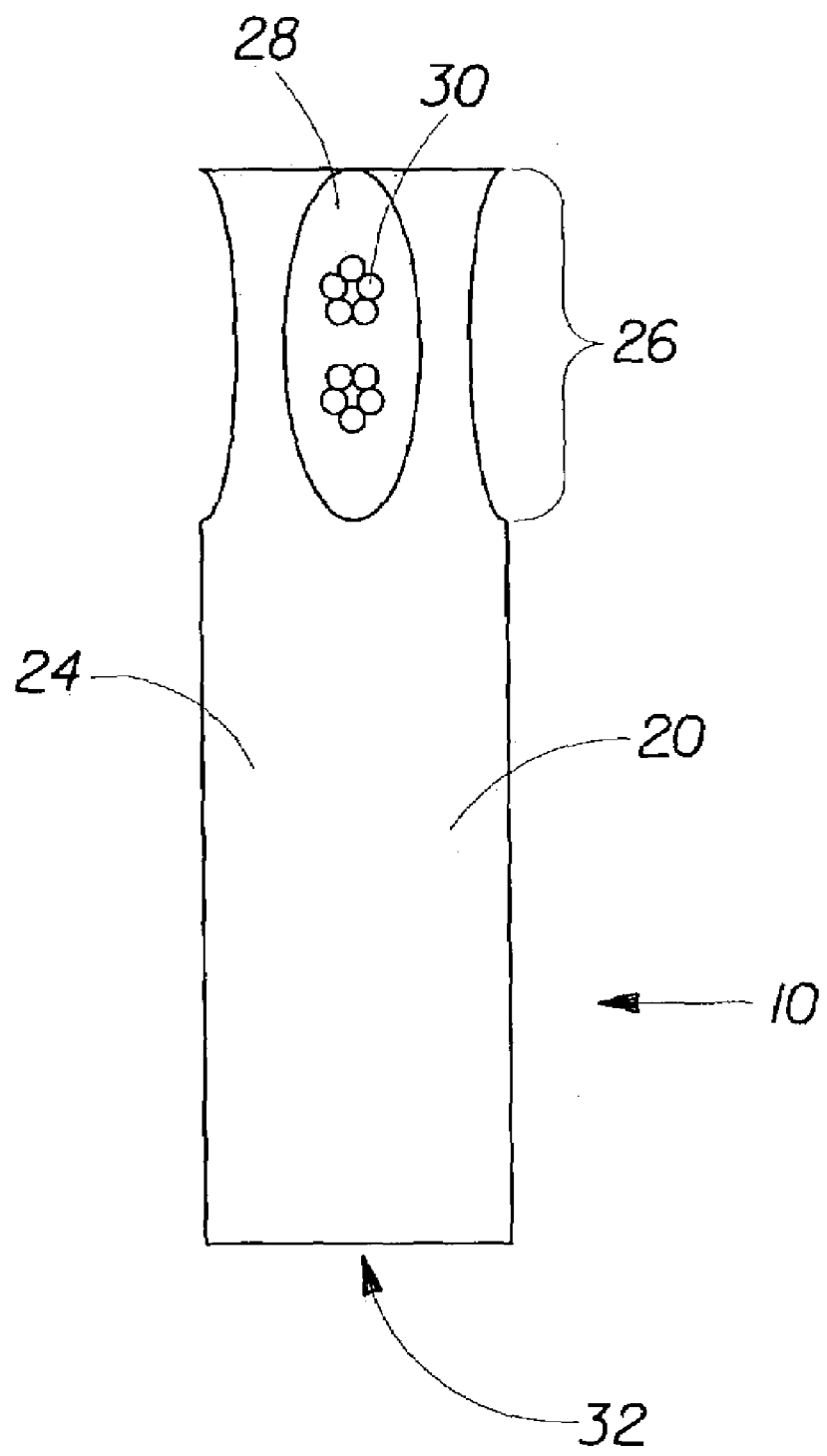
FIG. 2 is a perspective view of the applicator of the present invention.

FIG. 1 and FIG. 2 show the tampon applicator of the present invention. The tampon applicator 10 includes an insertion member 20 adapted to house an absorbent tampon and a plunger 22. The insertion member has an outer surface 24 and a fingergrip region 26 disposed about the outer surface 24. The fingergrip region 26 comprises an indention region 28 having a depth dimension X. The indention region 28 comprises raised portions 30 having a height dimension Y, the height dimension Y being less than or equal to the depth dimension X. When a consumer inserts the insertion member 20 into her vaginal cavity, her fingers and/or thumb are urged towards the insertion end 32 due to frictional forces between the insertion member 20 and the walls of the body cavity. The combination of the indention region 28 and the raised portions 30 and their respective dimensions in relation to each other provides a secure hold and improved handling of the applicator during insertion.

The insertion member 20 is in the form of a spirally wound, convolutely wound or longitudinally seamed hollow tube, which is formed from paper, paperboard, cardboard or a combination thereof. The insertion member 20 may also be injection molded or formed from flexible plastic, such as thermoformed from plastic sheet or folded or wound from plastic film. The insertion member 20 may also be formed from a combination of paper and plastic. The insertion member 20, also commonly referred to as an outer tube, is fairly rigid and has a relatively small diameter of about 10 millimeters to about 20 millimeters. The insertion member 20 has a wall with a predetermined thickness of about 0.1 millimeters to about 0.7 millimeter. The wall can be constructed from a single ply of material or be formed from two or more plies that are bonded together to form a laminate.

The use of two or more plies or layers is preferred for it enables the manufacturer to use certain materials in the various layers that can enhance the performance of the tampon applicator 10. When two or more plies are utilized, all the plies can be spirally wound, convolutely wound or longitudinally seamed to form an elongated cylinder. For example, in some embodiments the wall can be constructed using a smooth thin ply of material on the outside or exterior surface that surrounds a coarser and possibly thicker ply. In embodiments where the wall contains at least three plies, the middle ply can be the thicker ply and the interior and exterior plies can be smooth and/or slippery to facilitate expulsion of the tampon and to facilitate insertion of the insertion member 20 into a woman's vagina, respectively. By sandwiching a thick, coarser ply of material between two thin, smooth plies, an inexpensive insertion member 20 can be provided which is very functional. The wall may contain one to four plies, although more plies can be utilized if desired. As well, the ends of the insertion member 20 can be lipped.

An adhesive, such as glue, or by heat, pressure, ultrasonics, etc, can hold the plies forming the wall together. The adhesive can be either water-soluble or water-insoluble. A water-soluble adhesive is typically used for environmental reasons in that the wall will quickly break apart when it is immersed in water. Such immersion will occur should the insertion member 20 be disposed of by flushing it down a toilet. Exposure of the insertion member 20 to a municipal's waste treatment plant wherein soaking in water, interaction with chemicals and agitation all occur, will cause the wall to break apart and evenly disperse in a relatively short period of time.

The inside diameter of the insertion member 20 is usually less than about 0.75 inches (about 19 mm) and may be about 0.394 inches (about 10 mm). Although the exterior diameter, of tampons does vary, most tampons utilized by women have an external of less than about 0.75 inches (about 19 mm). The measure of external diameter excludes the indention region 32 of the fingergrip region 26. However, if one desires to use this invention to administer medication to an animal, such as a farm animal or other mammal, larger size tampons, which would require insertion members with a larger diameter, could be used.

Alternatively, the material can be overlapped into a tubular configuration. Spirally or convolutely winding the insertion member 20 into a cylindrical tube is especially advantageous when the insertion member 20 is formed from a laminate. In the case of other tube construction methods such as fiber or plastic molding, or integral tube forming (e.g. thermoforming plastic) no seams will be present and the corrugations could optionally be formed as part of the tube molding or forming process.

The insertion member 20 is sized and configured to house an absorbent tampon. As stated above, the insertion member 20 should have a substantially smooth exterior surface that will facilitate insertion of the insertion member 20 into a woman's vagina. When the exterior surface is smooth and/or slippery, the insertion member 20 will easily slide into a woman's vagina without subjecting the internal tissues of the vagina to abrasion. The insertion member 20 can be coated to give it a high slip characteristic. Wax, polyethylene, a combination of wax and polyethylene, cellophane, clay, mica, and other lubricants are representative coatings that can be applied to the insertion member 20 to facilitate comfortable insertion.

The insertion member 20 has an outer surface 24 and a fingergrip region 26 disposed about the outer surface 24. The insertion member 20 has an insertion end 32 opposed to a fingergrip region 26. The fingergrip region 26 comprises an indention region 28 having a depth dimension X. The indention region 28 may be any geometric shape known including but not limited to oval, circular, rectangular, trapezoidal, triangular, hemispherical and mixtures thereof. In some embodiments, the depth dimension X may range from about 1 mm to about 10 mm as measured from the outer surface of the insertion member 20 to the lowest point of the indention region 28. In some embodiments, the depth dimension X may range from about 2 mm to about 5 mm as measured from the outer surface of the insertion member 20 to the lowest point of the indention region 28. In other embodiments, the depth dimension X may range from about 2.5 mm to about 3.5 mm as measured from the outer surface of the insertion member 20 to the lowest point of the indention region 28.

The indention region 28 comprises raised portions 30 having a height dimension Y, the height dimension Y being less than or equal to the depth dimension X. The raised portions 30 may be any three-dimensional geometric shape known including but not limited to ovals, circles, rectangles, trapezoids, triangles, cones, alphabet letters, and mixtures thereof. In all embodiments, the height dimension Y is less than or equal to the depth dimension X. In some embodiments, the height dimension Y is less than the depth dimension X. In some embodiments, the depth dimension Y ranges from about to about 0.1 mm to about 10 mm as measured from the base 34 to highest point 36 of the individual raised portion that is adjacent to the outer surface 24 of the insertion member 20. In some embodiments, the depth dimension Y ranges from about to about 0.2 mm to about 5 mm as from the base 34 to highest point 36 of the individual raised portion. In other embodiments, the depth dimension Y ranges from about to about 0.5 mm to about 2.5 mm from the base 34 to highest point 36 of the individual raised portion.

The number of the raised portions 30 may range from 1 to 200 depending on the size of both the indention region 28 and the raised portions 30. The individual raised portions 30 may be formed to have essentially identical size and shape as compared to other individual raised portions 30. Alternatively, the individual raised portions 30 may be formed to have to various sizes and shapes as compared to other individual raised portions 30. The raised portions 30 may be arranged randomly or in a pattern. For example, the raised portions 30 can be arranged to form any three-dimensional geometric pattern known including but not limited to flowers, ovals, circles, rectangles, trapezoids, triangles, cones, alphabet letters, and mixtures thereof. Alternatively, these raised portions 30 may be randomly arranged so that the multiplicity of the molded or attached dimples may comprise merely a surface roughness in no apparent pattern. In addition, raised portions 30 may be arranged such that the areas between the raised portions 30 may form any geometric pattern known including but not limited to flowers, ovals, circles, rectangles, trapezoids, triangles, cones, alphabet letters, and mixtures thereof.

All documents cited in the Detailed Description of the Invention are, are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A tampon applicator comprising:
   an insertion member adapted to house an absorbent tampon and receive a plunger;
   said insertion member having an outer surface and a fingergrip region extending inwardly from said outer surface and disposed between distal and proximal ends of said insertion member;
   said fingergrip region comprising an indention region having a depth dimension X, wherein said depth dimension X is measured from the outer surface of insertion member to lowest point of indentation region;
   said indention region comprising protruding, three-dimensional raised portions that are positioned within said indentation region and having a height dimension Y, wherein said height dimension Y is measured from base to highest point of individual raised portion that is adjacent to outer surface of insertion member said height dimension Y being less than or equal to said depth dimension X.

2. The tampon applicator according to claim 1 wherein said tampon applicator is comprised of paper.

3. The tampon applicator according to claim 1 wherein said depth dimension X is from about 1 mm to about 10 mm.

4. The tampon applicator according to claim 1 wherein said height dimension Y is from about 0.1 mm to about 10 mm.

5. The tampon applicator according to claim 1 wherein the tampon applicator is comprised of plastic.

6. The tampon applicator according to claim 1 wherein the indention region has a shape selected from the group consisting of oval, circular, rectangular, trapezoidal, triangular, hemispherical and mixtures thereof.

7. The tampon applicator according to claim 1 wherein the raised portions have a shape selected from the group consisting of ovals, circles, rectangles, trapezoids, triangles, cones, alphabet letters, and mixtures thereof.

8. The tampon applicator according to claim 1 wherein the raised portions are arranged in a pattern.

9. A tampon applicator comprising:
   an insertion member adapted to house an absorbent tampon and receive a plunger;
   said insertion member having an outer surface and a fingergrip region extending inwardly from said outer surface and disposed between distal and proximal ends of said insertion member;
   said fingergrip region comprising an indention region having a depth dimension X, wherein said depth dimension X is measured from the outer surface of insertion member to lowest point of indentation region;
   said indention region comprising protruding, three-dimensional raised portions that are positioned within said indentation region and having a height dimension Y, wherein said height dimension Y is measured from base to highest point of individual raised portion that is adjacent to outer surface of insertion member said height dimension Y being less than said depth dimension X.

10. The tampon applicator according to claim 9 wherein said tampon applicator is comprised of paper.

11. The tampon applicator according to claim 9 wherein said depth dimension X is from about 2 mm to about 5 mm.

12. The tampon applicator according to claim 9 wherein said height dimension Y is from about 0.2 mm to about 5.0 mm.

13. The tampon applicator according to claim 9 wherein the raised portions are arranged in a pattern.

14. The tampon applicator according to claim 9 wherein the patterns are selected from the group consisting of flowers, ovals, circles, rectangles, trapezoids, triangles, cones, alphabet letters, and mixtures thereof.

15. A tampon applicator comprising:
   an insertion member adapted to house an absorbent tampon and receive a plunger;
   said insertion member having an outer surface and a fingergrip region extending inwardly from said outer surface and disposed between distal and proximal ends of said insertion member;
   said fingergrip region comprising an indention region having a depth dimension X, wherein said depth dimension X is measured from the outer surface of insertion member to lowest point of indentation region;
   said indention region comprising protruding, three-dimensional raised portions that are positioned within said indentation region and having a height dimension Y, wherein said height dimension Y is measured from base to highest point of individual raised portion that is adjacent to outer surface of insertion member said height dimension Y being less than or equal to said depth dimension X;

wherein said tampon applicator is comprised of paper.

16. The tampon applicator according to claim 15 wherein said depth dimension X is from about 2.5 mm to about 3.5 mm.

17. The tampon applicator according to claim 15 wherein said height dimension Y is from about 0.5 mm to about 2.5 mm.

18. The tampon applicator according to claim 15 wherein the indention region has a shape selected from the group consisting of oval, circular, rectangular, trapezoidal, triangular, hemispherical and mixtures thereof.

19. The tampon applicator according to claim 15 wherein the raised portions have a shape selected from the group consisting of ovals, circles, rectangles, trapezoids, triangles, cones, alphabet letters, and mixtures thereof.

20. The tampon applicator according to claim 15 wherein the raised portions are arranged in a pattern selected from the group consisting of flowers, ovals, circles, rectangles, trapezoids, triangles, cones, alphabet letters, and mixtures thereof.

* * * * *